United States Patent
Noda et al.

(10) Patent No.: US 10,323,266 B2
(45) Date of Patent: Jun. 18, 2019

(54) ANTIMICROBIAL SUSCEPTIBILITY TESTING DEVICE, ANTIMICROBIAL SUSCEPTIBILITY TESTING KIT, AND ANTIMICROBIAL SUSCEPTIBILITY TESTING METHOD

(71) Applicant: Hitachi, Ltd., Tokyo (JP)

(72) Inventors: Hideyuki Noda, Tokyo (JP); Hiroko Tada, Tokyo (JP); Chihiro Uematsu, Tokyo (JP); Masahiro Okanojo, Tokyo (JP)

(73) Assignee: HITACHI, LTD., Tokyo (JP)

( * ) Notice: Subject to any disclaimer, the term of this patent is extended or adjusted under 35 U.S.C. 154(b) by 78 days.

(21) Appl. No.: 15/557,017

(22) PCT Filed: Mar. 17, 2015

(86) PCT No.: PCT/JP2015/057876
§ 371 (c)(1),
(2) Date: Sep. 8, 2017

(87) PCT Pub. No.: WO2016/147313
PCT Pub. Date: Sep. 22, 2016

(65) Prior Publication Data
US 2018/0057853 A1 Mar. 1, 2018

(51) Int. Cl.
| | | |
|---|---|---|
| *C12Q 1/18* | (2006.01) | |
| *C12Q 1/66* | (2006.01) | |
| *C12M 1/00* | (2006.01) | |
| *C12M 1/12* | (2006.01) | |
| *C12M 1/34* | (2006.01) | |
| *C12M 3/00* | (2006.01) | |
| *G01N 21/76* | (2006.01) | |

(52) U.S. Cl.
CPC .............. *C12Q 1/18* (2013.01); *C12M 1/34* (2013.01); *C12M 23/44* (2013.01); *C12M 25/06* (2013.01); *C12M 29/00* (2013.01); *C12M 45/06* (2013.01); *C12M 45/20* (2013.01); *C12Q 1/66* (2013.01); *G01N 21/763* (2013.01)

(58) Field of Classification Search
CPC ........ A01N 35/06; A01N 43/30; A01N 51/00; A01N 53/00; A01N 25/06; A01N 25/30; A61B 17/00491; A61B 17/0057; A61B 17/12022; A61B 17/12118; A61B 17/12181; A61B 17/3468; A61B 18/02; A61B 18/04; A61B 18/1492; A61B 18/18; A61B 18/245; A61B 2017/00411; A61B 2017/00544; A61B 2017/0065; A61B 2017/00809; A61B 2017/00876; A61B 2017/1205; A61B 2017/22001; A61B 2018/00005; A61B 2018/00023; A61B 2018/00345; A61B 2018/00517; A61B 2018/00541; A61B 2018/00577; A61B 2018/00595; A61B 2018/00982; A61B 2018/1861; A61B 2218/002; A61F 2002/9528; A61F 2210/009; A61F 2/013; A61F 2/82; A61F 2/95; A61M 37/00; A61N 2005/1011; A61N 7/00; C12M 1/34; C12M 23/44; C12M 25/06; C12M 29/00; C12M 45/06; C12M 45/20; C12Q 1/18; C12Q 1/66; G01N 21/763
See application file for complete search history.

(56) References Cited

U.S. PATENT DOCUMENTS

2014/0342386 A1   11/2014   Okanojo et al.

FOREIGN PATENT DOCUMENTS

| JP | S61-166391 A | 7/1986 |
|---|---|---|
| JP | H05-084096 A | 4/1993 |
| JP | H08-304402 A | 11/1996 |
| JP | 2004-313028 A | 11/2004 |
| WO | 2013084772 A1 | 6/2013 |

OTHER PUBLICATIONS

International Search Report and Written Opinion for PCT App No. PCT/JP2015/057876 dated Jun. 16, 2015, 9 pgs.

*Primary Examiner* — Deborah K Ware
(74) *Attorney, Agent, or Firm* — Procopio, Cory, Hargreaves & Savitch LLP (57) ABSTRACT

Provided is a antimicrobial susceptibility testing device, including: an ATP examination culture plate that includes a reaction vessel, a reagent holding parts for holding reagents to be supplied to the reaction vessel, and a culture solution holding part for holding a culture solution to be supplied to the reaction vessel, and has plural layers that can be joined and separated; a gas feeding path for feeding a gas into the ATP examination culture plate; a heater; an optical detection unit; and a determination unit for determining sensitivity of a bacterial strain contained in the culture solution to a drug based on a detection result of the optical detection unit, wherein when the plural layers of the ATP examination culture plate are joined, at least the culture solution holding part and the reaction vessel are in a sealed state while communicating with each other.

15 Claims, 5 Drawing Sheets

ANTIMICROBIAL SUSCEPTIBILITY TESTING DEVICE, ANTIMICROBIAL SUSCEPTIBILITY TESTING KIT, AND ANTIMICROBIAL SUSCEPTIBILITY TESTING METHOD

CROSS-REFERENCE TO RELATED APPLICATIONS

This application is a U.S. National Stage entry of PCT Application No. PCT/JP2015/057876, filed on Mar. 17, 2015, the contents of which are incorporated herein by reference.

TECHNICAL FIELD

The present invention relates to a testing device and a testing kit for performing an antimicrobial susceptibility test of a bacterium, and an antimicrobial susceptibility testing method.

BACKGROUND ART

With increase of the mortality due to infectious diseases and appearance of drug resistance bacteria, speeding-up of antimicrobial susceptibility tests of infectious disease-causing bacteria is attracting attentions.

Conventionally, antimicrobial susceptibility tests have been implemented based on a culture method. An antimicrobial susceptibility test based on a culture method is conducted according to the following procedure. First, a specimen, such as blood, pharynx wiping liquid, and sputum, is collected from a patient of an infectious disease. Isolation culture is then performed for a whole day in order to obtain the infectious disease-causing bacterium as a single colony from the specimen containing indigenous bacteria together. The bacteria forming the single colony are prepared into a prescribed concentration and dispensed into vessels in which a drug or antibody of various kinds and various concentrations are placed, and the antimicrobial susceptibility culture is conducted for a whole day. After culturing the bacteria, a result of the antimicrobial susceptibility test of the infectious disease-causing bacterium is obtained based on the presence or absence of the growth of the bacteria, and according to the result, proper drug dosage is applied to the patient. Accordingly, the proper dosage for the patient of the infectious disease is started at three or more days after the collection of the specimen.

On the other hand, as a method for rapidly performing an antimicrobial susceptibility test, an ATP bioluminescence method using, as a measure of the growth of the bacteria, variation of adenosine triphosphate (ATP) which is present in bacteria as an energy source is mentioned. In the ATP method, ATP present in bacteria as an energy source is detected by utilizing luciferase which is an enzyme derived from firefly. Since luciferase oxidizes luciferin, which is a substrate, in the presence of ATP and $Mg^{2+}$ in the bacteria and the amount of the thus-generated luminescence is proportional to the ATP amount, the growth of the bacteria can be estimated from the variation in the amount of luminescence.

A process for determining the number of bacteria by the use of the ATP method is disclosed, for example, in PTL 1. PTL 1 discloses a technique in which viable cells are counted by the ATP measurement and the total cells are counted by a DNA method, followed by subtracting the viable cell number from the total cell number to obtain the viable cell number and the dead cell number.

CITATION LIST

Patent Literature

PTL 1: JP-A-08-304402

SUMMARY OF INVENTION

Technical Problem

The infectious disease-causing bacteria to be subjected to antimicrobial susceptibility tests are roughly classified into aerobic bacteria, facultative anaerobic bacteria, and obligate anaerobic bacteria. Among them, aerobic bacteria and facultative anaerobic bacteria can grow in the presence of oxygen, but obligate anaerobic bacteria die when exposed to oxygen.

Since aerobic bacteria and facultative anaerobic bacteria can be cultured in a usual atmosphere, it is possible to configure a device for an antimicrobial susceptibility test by the ATP method without taking into account exposure or non-exposure of the culture solution to oxygen.

Meanwhile, culture of obligate anaerobic bacteria has to be conducted in a state where exposure to oxygen is avoided. In addition, in measurement by the ATP method, not only the culture but also a reagent reaction, for example, for extracting ATP in bacterial cells is required. These steps have to be conducted in a state where exposure to oxygen is avoided. Thus, for conducting the entire antimicrobial susceptibility test in an automated device, all the steps from culture to measurement have to be conducted in a state where the culture solution is not exposed to oxygen. For this reason, with respect to obligate anaerobic bacteria, it has been difficult to develop a device and a system for performing a antimicrobial susceptibility test in an oxygen-existing environment.

The present invention has an object to provide an antimicrobial susceptibility testing device and an antimicrobial susceptibility testing method by which a antimicrobial susceptibility test by an ATP method can be implemented for both of aerobic bacteria and anaerobic bacteria.

Solution to Problem

A preferred embodiment of the present invention is an antimicrobial susceptibility testing device, including: an ATP examination culture plate that includes a reaction vessel, a reagent holding part for holding a reagent to be supplied to the reaction vessel, and a culture solution holding part for holding a culture solution to be supplied to the reaction vessel, and has plural layers that can be joined and separated; a gas feeding path for feeding a gas into the ATP examination culture plate; a heater for heating the culture solution holding part; an optical detection unit for detecting luminescence inside the reaction vessel; and a determination unit for determining sensitivity of a bacterial strain contained in the culture solution to a drug based on a detection result of the optical detection unit, wherein when the plural layers in the ATP examination culture plate are joined, at least the culture solution holding part and the reaction vessel are in a sealed state while communicating with each other.

Furthermore, another preferred embodiment of the present invention is an antimicrobial susceptibility testing kit; including an ATP examination culture plate that includes a reaction vessel, a reagent holding part for holding a reagent to be supplied to the reaction vessel, and a culture solution holding part for holding a culture solution to be supplied to the reaction vessel, and has plural layers that can be joined and separated; and a gas feeding path for feeding a gas into the ATP examination culture plate, wherein when the plural layers in the ATP examination culture plate are joined, at least the culture solution holding part and the reaction vessel are in a sealed state while communicating with each other.

Furthermore, another preferred embodiment of the present invention is an antimicrobial susceptibility testing method, including: providing an ATP examination culture plate that includes a reaction vessel, a reagent holding part that holds a reagent to be supplied to the reaction vessel, and a culture solution holding part for holding a culture solution to be supplied to the reaction vessel, and has plural layers, and bringing at least the culture solution holding part and the reaction vessel of the ATP examination culture plate into a sealed state in a manner that the culture solution holding part and the reaction vessel communicate with each other; feeding a gas from a gas feeding part into the ATP examination culture plate in which the plural layers are joined; heating the culture solution holding part in the sealed state by a heater to culture a bacterial suspension obtained by mixing a bacterium and a drug; supplying a culture solution obtained by culturing the bacterial suspension into the reaction vessel in the sealed state, while supplying the reagent from the reagent holding part into the reaction vessel; detecting luminescence inside the reaction vessel holding a reaction solution of the culture solution and the reagent by an optical detection unit; and determining the sensitivity of the bacterial strain contained in the culture solution to the drug by a determination unit based on the detection result of the optical detection unit.

Advantageous Effects of Invention

According to the present invention, an antimicrobial susceptibility test by an ATP method can be performed for both of aerobic bacteria and anaerobic bacteria.

DESCRIPTION OF EMBODIMENTS

Hereinunder, a suitable embodiment of the present invention will be illustrated in detail by Examples with reference to the drawings. However, unless otherwise noted, the dimensions, materials, shapes, other relational positions, and the like of components described in Examples are not intended to limit the scope of the invention thereto, and are merely examples for illustration.

Figure 1:
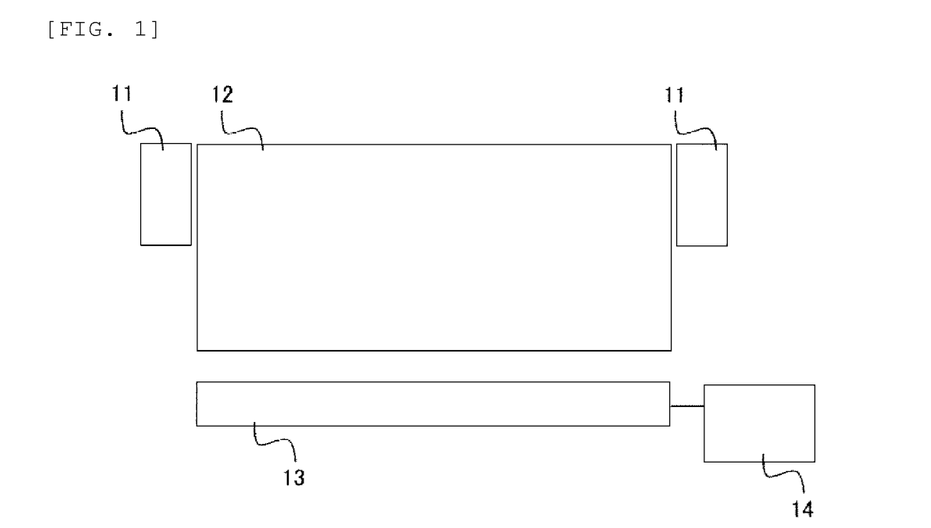
FIG. 1 It is a schematic diagram showing a configuration of an antimicrobial susceptibility testing device according to an embodiment.

FIG. 1 is a schematic diagram showing a configuration of an antimicrobial susceptibility testing device according to an embodiment. The antimicrobial susceptibility testing device is provided with an ATP examination culture plate 12, heaters 11, an optical detector 13, and a determination unit 14.

In the example shown in FIG. 1, the heaters 11 are provided so as to be adjacent to the ATP examination plate 12 in the vicinity of a surface thereof opposite to the surface on which the optical detector 13 is placed. Incidentally, the shape and the number of the heaters 11 are not particularly limited, and the installation position may also be appropriately varied according to the usage mode.

Figure 2:
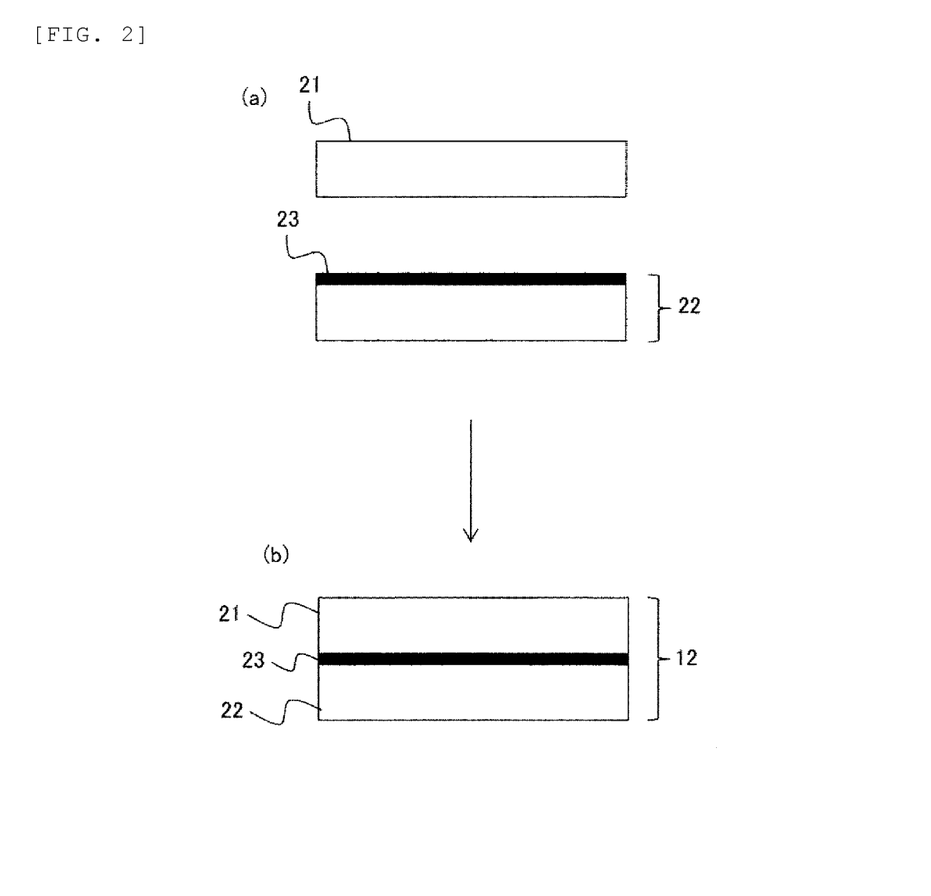
FIG. 2 It is a diagram for explaining a configuration of an ATP examination culture plate shown in FIG. 1.

FIG. 2 is a diagram for explaining a configuration of the ATP examination culture plate 12 shown in FIG. 1. As shown in FIG. 2(a), the ATP examination culture plate 12 is composed of two layers of a first plate 21 and a second plate 22. On the top surface of the second plate 22, a joint portion 23 for joining the second plate 22 with the first plate 21 is formed.

The first plate 21 and the second plate 22 are configured to be freely joined (see FIG. 2(b)) and separated (see FIG. 2(a)) via the joint portion 23.

Figure 3:
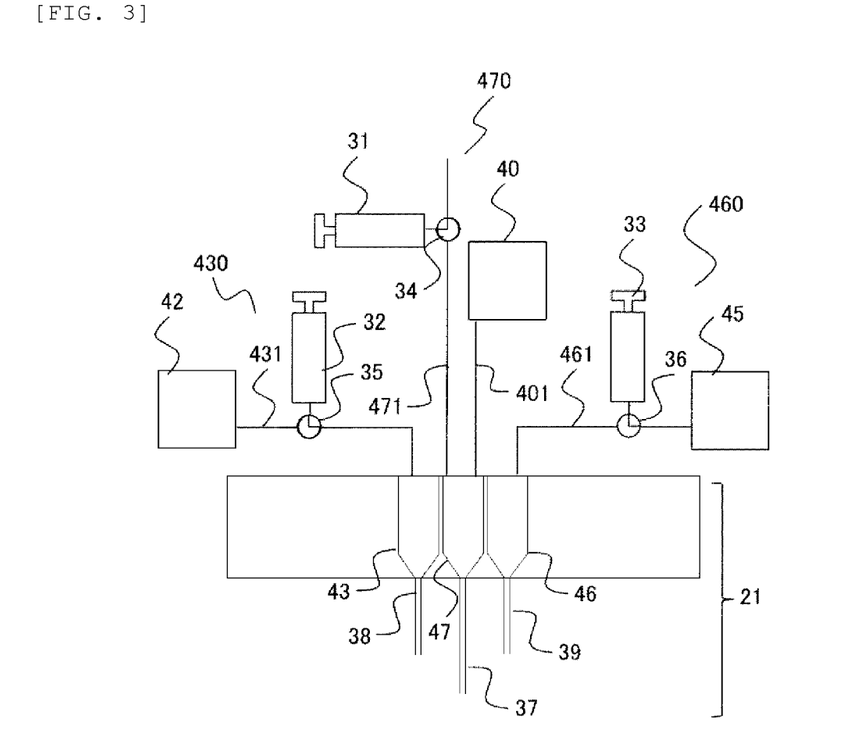
FIG. 3 It is a diagram showing an internal structure of a first plate shown in FIG. 2 along with a peripheral structure of the first plate.
Figure 4:
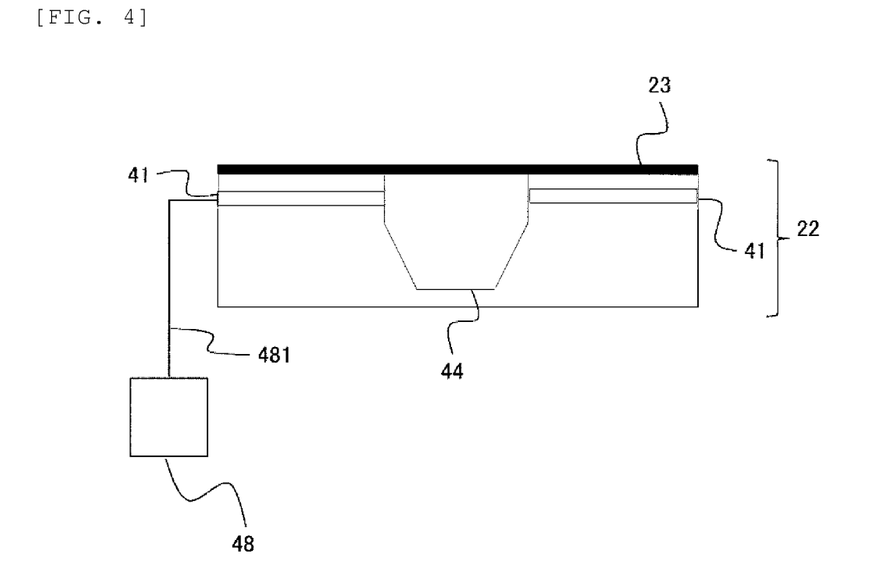
FIG. 4 It is a cross section showing an internal structure of a second plate shown in FIG. 2.

FIG. 3 is a diagram showing an internal structure of the first plate 21 shown in FIG. 2, along with a peripheral structure of the first plate 21, and FIG. 4 is a cross section showing a configuration of the second plate 22 shown in FIG. 2.

The first plate 21 includes a culture solution holding part 47, an extraction liquid holding part 43, and a luminescence reagent holding part 46 (see FIG. 3), and the second plate 22 includes a reaction vessel 44 formed as a bottomed aperture (see FIG. 4). Detailed configurations of the first plate 21 and the periphery thereof and a detailed configuration of the second plate 22 will be described later.

Figure 5:
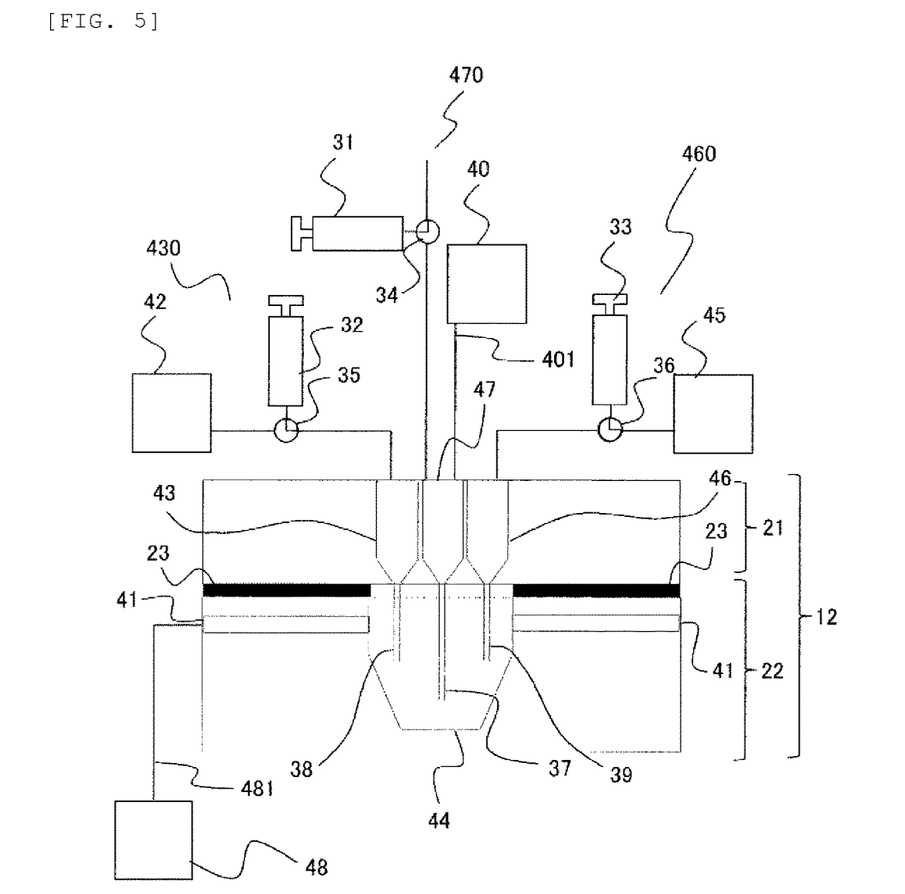
FIG. 5 It is a diagram showing a state where the first plate and the second plate are joined, along with the peripheral structure of the first plate.

As shown in FIG. 5, the first plate 21 is configured so that, by being joined with the second plate 22 via the joint portion 23, the culture solution holding part 47, the extraction liquid holding part 43, and the luminescence reagent holding part 46 in the first plate 21 fit with the reaction vessel 44 in the second plate 22.

Hereinunder, the first plate 21 and the peripheral structure thereof will be described in detail by FIG. 3.

As shown in FIG. 3, a culture solution supplying unit 470 includes the culture solution holding part 47 that holds a culture solution to be supplied to the reaction vessel 44, a nozzle 37 that is connected to one end of the culture solution holding part 47, and a syringe 31 that is connected to the other end side of the culture solution holding part 47 via a connection pipe 471.

Into the culture solution holding part 47, a bacterial suspension in which a bacterium to be subjected to a antimicrobial susceptibility test which has been isolated from a specimen and a drug such as an antibody are mixed is sucked from an outside container through the nozzle 37 by switching the flow path of a valve 34 provided at the tip of the syringe 31. The bacterial suspension that has been sucked into the culture solution holding part 47 is cultured at a prescribed temperature to become a culture solution, which is then supplied again through the nozzle 37 into the reaction vessel 44 in the second plate 22.

To the culture solution holding part 47, a first gas feeding part 40 is connected via a feeding pipe 401. The first gas feeding part 40 includes a gas concentration meter and a gas pressure controlling mechanism so that the inside of the culture solution holding part 47 can be controlled into a gas atmosphere that is suited to the culture of the bacterial cells to be subjected to the antimicrobial susceptibility test.

A extraction liquid supplying unit 430 includes the extraction liquid holding part 43 that holds an extraction liquid to be supplied to the reaction vessel 44, a nozzle 38 that is connected to one end of the extraction liquid holding part 43, an extraction liquid bottle 42 that is connected to the other end side of the extraction liquid holding part 43 via a connection pipe 431, and a syringe 32 provided between the extraction liquid bottle 42 and the extraction liquid holding part 43.

The extraction liquid is a reagent for extracting ATP from bacteria, and the extraction liquid contained in the extraction liquid bottle 42 is charged in the extraction liquid holding part 43 by switching the flow path of a valve 35 provided at the tip of the syringe 32, passes through the nozzle 38, and supplied into the reaction vessel 44 in the second plate 22.

A luminescence reagent supplying unit 460 includes the luminescence reagent holding part 46 that holds a luminescence reagent to be supplied into the reaction vessel 44, a nozzle 39 that is connected to one end of the luminescence reagent holding part 46, a luminescence reagent bottle 45 that is connected to the other end side of the luminescence reagent holding part 46 via a connection pipe 461, and a syringe 33 that is provided between the luminescence reagent bottle 45 and the luminescence reagent holding part 46.

The luminescence reagent is a reagent that emits light by being mixed with ATP extracted from cells of a bacterium or the like, and the luminescence reagent contained in the luminescence reagent bottle 45 is charged in the luminescence reagent holding part 46 by switching the flow path of a valve 36 provided at the tip of the syringe 33, passes through the nozzle 39, and is supplied into the reaction vessel 44 in the second plate 22.

The nozzle 37 connected to the culture solution holding part 47 is provided so as to be longer than the nozzle 38 connected to the extraction liquid holding part 43 and the nozzle 39 connected to the luminescence reagent holding part 46.

By this configuration, when the bacterial suspension is sucked from the container outside the ATP examination culture plate 12, without bringing the tips of the nozzle 38 and the nozzle 39 into contact with the bacterial suspension, only the tip of the nozzle 37 can be brought into contact with the bacterial suspension, whereby the workability during sucking the bacterial suspension from the nozzle 37 into the culture solution holding part 47 can be enhanced.

When the first plate 21 shown in FIG. 3 as described above is joined with the second plate 22 via the joint portion 23, as shown in FIG. 5, the nozzle 37, the nozzle 38, and the nozzle 39 are inserted into the reaction vessel 44, and the reaction vessel 44 fits with the culture solution holding part 47, the extraction liquid holding part 43, and the luminescence reagent holding part 46.

Thus, the reaction vessel 44, the culture solution holding part 47, the extraction liquid holding part 43, and the luminescence reagent holding part 46 come in a sealed state, in a state where the reaction vessel 44 and the culture solution holding part 47, the extraction liquid holding part 43, and the luminescence reagent holding part 46 communicate with each other by the nozzles 37, 38, and 39.

Incidentally, in the example shown in FIG. 3 and FIG. 5, a configuration in which one extraction liquid holding part 43 and one luminescence reagent holding part 46 are inserted into one reaction vessel 44 is shown. However, according to the inspection item of the antimicrobial susceptibility test, a configuration in which plural extraction liquid holding parts 43 and plural luminescence reagent holding parts 46 are inserted is possible. In this case, the extraction liquid holding part 43 and the luminescence reagent holding part 46 may have similar shapes, or may have different shapes from each other to the extent that the parts can be placed in the first plate 21.

As shown in FIG. 4, the reaction vessel 44 formed in the second plate 22 holds the culture solution supplied from the culture solution holding part 47, the extraction liquid supplied from the extraction liquid holding part 43, and the luminescence reagent supplied from the luminescence reagent holding part 46, which are in the first plate 21, and the culture solution, the extraction liquid, and the luminescence reagent supplied from the first plate 21 are mixed in the reaction vessel 44.

As shown in FIG. 5, the first plate 21 and the second plate 22 are joined with each other with the nozzles 37, 38, and 39 inserted in the reaction vessel 44. For this reason, the reaction vessel 4 is provided so as to have a depth that allows the first plate 21 and the second plate 22 to be joined with each other with the nozzle 37, 38, and 39 inserted therein.

The second plate 22 is required to have transmittance at least in the bottom portion of the reaction vessel 44 so that luminescence detection can be performed by the optical detector 13. For this reason, as for the second plate 22, for example, it is preferred that the second plate 22 itself is made of a transparent material since optical detection by the optical detector 13 is then possible. In addition, when the second plate 22 is made of a material that does not have transmittance, by cutting out an area in the bottom of the reaction vessel 44 and fitting a member made of a transmitting material into the cut-out portion, optical detection by the optical detector 13 becomes possible.

Incidentally, the optical detector 13 is not particularly limited, but, for example, a photomultiplier tube, a CCD camera, a photodiode, and the like may be used.

A gas feeding path 41 is provided through the second plate 22 so as to communicate with the reaction vessel 44. A second gas feeding part 48 is connected to the gas feeding path 41 via a feeding pipe 481, and a gas fed from the second gas feeding part 48 is fed to the reaction vessel 44 through the gas feeding path 41.

The second gas feeding part 48 has a gas controlling mechanism, such as a gas concentration meter and a gas pressure controlling mechanism, and can control the inside of the reaction vessel 44 into a gas atmosphere that is suited to the kind of the bacterial cells to be subjected to the antimicrobial susceptibility test.

The joint portion 23 is formed so as to cover the whole top surface of the second plate 22 including the opened end side of the reaction vessel 44. By this, the gas atmosphere inside the reaction vessel 44 is maintained by the joint portion 23.

As shown in FIG. 5, since the first plate 21 and the second plate 22 are joined with the nozzles 37, 38, and 39 inserted in the reaction vessel 44, it is preferred that the connection portion 23 is provided with, for example, apertures having similar diameters to those of the nozzles 37, 38 and 39 so that the nozzles can be inserted into the reaction vessel 44.

As a material of the joint portion 23, any material that makes it possible to join the first plate 21 and the second plate 22 and is impervious to gas can be used with no limitation. Specifically, for example, a silicone resin and a thermosetting resin may be used.

Incidentally, the joint portion 23 may be appropriately provided with an O-ring or the like for improving the joint of the first plate 21 and the second plate 22.

In the example shown in FIGS. 4 and 5, a configuration in which a single reaction vessel 44 is provided in the second plate 22 and the single reaction vessel 44 is connected to the gas feeding path 41 is shown. However, the antimicrobial susceptibility testing device of the present invention may have a configuration in which plural reaction vessels 44 are provided in the second plate 22 and the plural reaction vessels 44 are connected to one gas feeding path 41.

Figure 6:
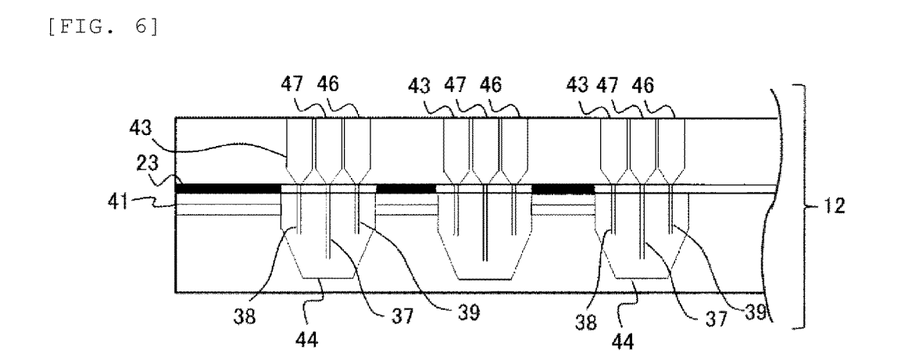
FIG. 6 It is a diagram showing a state where a second plate provided with plural reaction vessels and a first plate are joined.

In this case, as shown in FIG. 6, the antimicrobial susceptibility testing device is configured so that one set of the culture solution holding part 47, the extraction liquid holding part 43, and the luminescence reagent holding part 46 fits with one reaction vessel 44 and that the first plate 21 and the second plate 22 are joined. Incidentally, in the periphery of the first plate 21, a similar configuration as in FIG. 3 is provided. In FIG. 6, however, the structure in the periphery of the first plate 21 is omitted.

In the antimicrobial susceptibility testing device described above, the ATP examination culture plate 12 and the gas feeding path 41 which is provided in the second plate 22 may be provided as a antimicrobial susceptibility testing kit.

That is, the antimicrobial susceptibility kit is configured to include: the first plate 21 that is provided with the culture solution holding part 47 having the nozzle 37, the extraction liquid holding part 43 having the nozzle 38, and the luminescence reagent holding part 46 having the nozzle 39; the second plate 22 that includes the reaction vessel 44; the joint portion 23 that joins the first plate 21 and the second plate 22; and the gas feeding path 41 that is provided in the second plate 22.

By this kit, for example, when the ATP examination culture plate 12 or the gas feeding path 41 is damaged, or deteriorated due to a long term use, the antimicrobial susceptibility testing kit can be exchanged as a unit.

Figure 7:
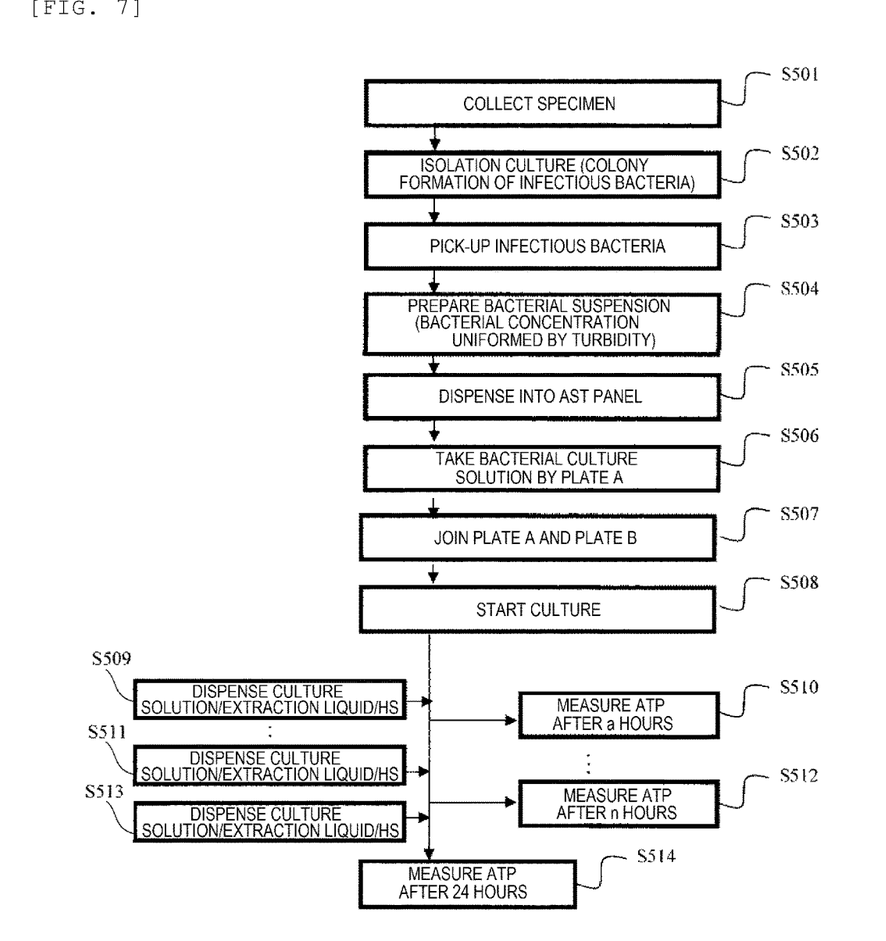
FIG. 7 It is a flow chart showing steps of an antimicrobial susceptibility test according to an embodiment.

FIG. 7 is a flow chart showing steps of the antimicrobial susceptibility test according to an embodiment. Incidentally, an infectious disease-causing bacterium to be measured by the present invention is not particularly limited as long as it contains ATP in the bacterial cell.

First, a specimen, such as blood, pharynx wiping liquid, and sputum, is collected from a patient of an infectious disease (S501), and then isolation culture is performed for a whole day in order to obtain the infectious disease-causing bacterium as a single colony from the specimen containing indigenous bacteria together (S502). After the isolation culture, the bacteria forming a single colony are collected (S503), prepared into a prescribed concentration (S504), and then dispensed into an AST panel in which a drug or antibody of various kinds and various concentration are placed (S505).
(AST Panel)

The material and the shape of the AST panel are not particularly limited, and a plate-like panel having plural wells on a flat surface is desirable, and, for example, a 96-well microplate in which 8 wells×12 wells=96 wells in total are integrated, a 384-well microplate in which 16 wells×24 wells=384 wells in total are integrated, or a 1532-well microplate in which 32 wells×48 wells=1532 wells in total are integrated, and the like may be used.

The drug or antibody applicable to the embodiment is not particularly limited. Examples include: a penicillin-type, a cephem-type, an aminoglycoside-type, a new quinolone-type, a fosfomycin-type, and other antibodies having a bactericidal action; and a macrolide-type, a tetracycline-type, and other drugs having a bacteriostatic action.

Specific examples include sulfonamide, aminobenzyl penicillin, and tetracycline. Incidentally, any drug, such as an antibody, that is suited to the bacterial strain may be appropriately selected and used, and the kind thereof is not particularly limited.

Next, a gas is fed from the first gas feeding part 40 through the feeding pipe 401 to the culture solution holding part 47 in the first plate 21, and while a gas atmosphere inside the culture solution holding part 47 is controlled, the bacterial suspension dispensed in the AST panel is taken using the first plate 21 in the ATP examination culture plate 12 (S506).

Specifically, the tip of the nozzle 37 of the culture solution holding part 47 is brought into contact with the bacterial suspension contained in a well of the AST panel and sucked by the syringe 31, thereby sucking the bacterial suspension in the AST panel into the culture solution holding part 47.

Subsequently, with the nozzle 37, 38, and 39 inserted in the reaction vessel 44, the first plate 21 and the second plate 22 of the ATP examination culture plate 12 are joined by the joint portion 23 (S507) to bring the culture solution holding part 47, the extraction liquid holding part 43, the luminescence reagent holding part 46, and the reaction vessel 44 into a sealed state (see, FIG. 5).

To the culture solution holding part 47 in the sealed state, the gas is further fed from the first gas feeding part 40, and while the gas atmosphere in the culture solution holding part 47 is controlled, the whole of the joined ATP examination culture plate 12 is heated by the heater 11 to conduct the antimicrobial susceptibility culture (S508). In parallel with this, into the reaction vessel 44 in the sealed state, a gas is fed from the second gas feeding part 48 via the gas feeding path 41 to control the gas atmosphere in the reaction vessel 44.

The heater 11 has a temperature sensor and a temperature controlling function, the temperature of the culture solution holding part 47 in the first plate 21 is controlled to a desired temperature according to the bacterial strain to be subjected to the antimicrobial susceptibility test, and the antimicrobial susceptibility culture of the culture solution which has been sucked into the culture solution holding part 47 is conducted (S508). The temperature during the culture is appropriately set according to the bacterial strain, and approximately 35 to 37° C.

After a certain period of time, the culture solution held in the culture solution holding part 47 in the first plate 21 is dispensed into the reaction vessel 44 with the atmosphere controlled by the nozzle 37 placed through the reaction vessel 44, subsequently, the extraction liquid in the extraction liquid holding part 43 is dispensed into the reaction vessel 44 by the nozzle 38 placed through the reaction vessel 44, and then, the luminescence reagent in the luminescence reagent holding part 46 is dispensed into the reaction vessel 44 by the nozzle 39 placed through the reaction vessel 44 (S509).

When the culture solution supplied into the reaction vessel 44 contains bacteria, ATP can be extracted from the bacteria by mixing the culture solution with the extraction liquid. The extraction liquid is not particularly limited as long as it can extract ATP from bacteria, and, for example, benzalkonium chloride, benzyl chloride, or formaldehyde can be used.

The mixture liquid containing ATP extracted from the bacteria is mixed with the luminescence reagent dispensed into the reaction vessel 44 to thereby emit light. The luminescence reagent is not particularly limited as long as it emits light by being mixed with ATP, and, for example, Lucifer HS set may be used.

After the luminescence reagent is dispensed, the amount of luminescence (ATP luminescence) in the reaction vessel 44 is detected by the optical detector 13 (S510). The luminescence measurement may be performed plural times. In the same manner as the above (S509), the culture solution, the extraction liquid, and the luminescence reagent are dispensed into the reaction vessel 44 (S511), and the amount of luminescence (ATP luminescence) in the luminescence vessel 44 is detected by the optical detector 13 (S512). Furthermore, the antimicrobial susceptibility culture is continued, and at 24 hours after the start of the culture, the culture solution, the extraction liquid, and the luminescence reagent are dispensed into the reaction vessel 44 (S513). Thus, the amount of luminescence (ATP luminescence) in the reaction vessel 44 at 24 hours after the start of the culture is detected (S514).

Incidentally, the timing of the luminescence measurement may be appropriately set. That is, by controlling the timing of dispensing the culture solution, the extraction liquid, and the luminescence reagent into the reaction vessel 44 by a controller (not shown) that controls the operations of the syringes 31, 32, and 33, it is possible to determine the sensitivity to a drag at a desired time. In this case, a antimicrobial susceptibility test may be conducted more flexibly.

Figure 8:
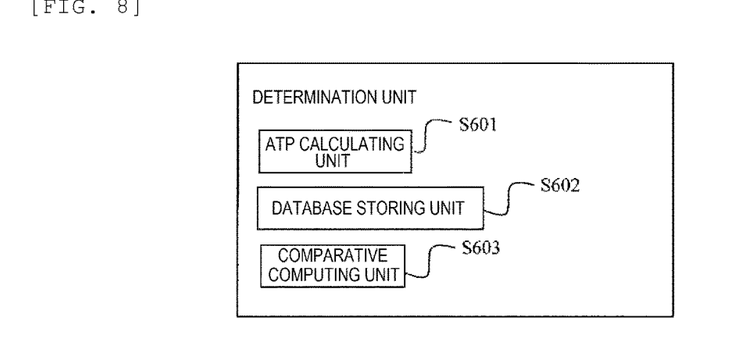
FIG. 8 It is a diagram showing an internal configuration of a determination unit.

FIG. 8 shows an internal configuration of the determination unit 14. The determination unit 14 is composed of an ATP calculating unit (S601), a database storing unit (S602), and a comparative computing unit (S603). Specifically, the results of the luminescence measurement obtained in the step (S510), the step (S512), or the step (S514) (see, FIG. 7) are stored in the ATP calculating unit (S601), and displayed as the results.

In addition, in the database storing unit (S602) for performing determination of the result of antimicrobial susceptibility (that is, determination of sensitivity of a bacterial strain contained in the culture solution to a drug), a calculation reference as a database that is created for each bacterial strain based on the previous detection results is stored.

If the bacterial strain has been identified, in the comparative computing unit (S603), the calculation reference corresponding to the bacterial strain is selected and read from the database storing unit (S602), and thus a proper value can be obtained as the threshold of the ATP luminescence and the determination of the antimicrobial susceptibility test can be more accurately achieved.

As described above, in the antimicrobial susceptibility test of the embodiment, the first plate 21 having the culture solution holding part 47 and the second plate 22 having the reaction vessel 44 are placed so that the first plate 21 and the second plate 22 can be joined and separated, and a gas feeding path for feeding a gas is provided in an ATP examination culture plate that is configured so that the culture solution holding part 47 and the reaction vessel 44 are in a sealed state when the first plate 21 and the second plate 22 are joined. With this configuration, culture of the bacterial cells, extraction of ATP from the bacteria, and detection of the luminescence can be continuously performed in a state where the inside of the culture solution holding part 47 and the reaction vessel 44 are controlled into a gas atmosphere suitable for the bacterial cells, in other words, in a state where the bacteria contained in the culture solution is not exposed to oxygen.

For this reason, not only an aerobic bacterium and a facultative anaerobic bacterium, but also an obligate anaerobic bacterium can be subjected to a test using the above device. Accordingly, regardless of aerobe or anaerobe, a antimicrobial susceptibility test for a wide variety of bacterial strain can be efficiently and easily performed.

Incidentally, the antimicrobial susceptibility test of the present invention is not limited to the aforementioned procedure, and can be conducted with the order appropriately changed. For example, in the aforementioned embodiment, in a state where the first plate 21 and the second plate 22 are separated, a bacterial suspension held outside the ATP culture plate 12 is sucked by the nozzle 37 into the culture solution holding part 47. However, the bacterial suspension can be sucked in a state where the first plate 21 and the second plate 22 are joined, for example.

In this case, the antimicrobial susceptibility test can be conducted using a device of a mode where a drug bottle (not shown) containing a drug and a bacterial liquid bottle (not shown) containing a liquid containing bacterial cells are connected to the culture solution holding part 47 (see, FIG. 3) and the syringe 31 is provided between the bottles and the culture solution holding part 47.

Specifically, in a state where the first plate 21 and the second plate 22 are joined, the drug contained in the drug bottle and the bacterial liquid contained in the bacterial liquid bottle are sucked by the syringe 31 and supplied once into the reaction vessel 44, and the drug and the bacterial liquid are mixed in the reaction vessel 44 to make a bacterial suspension, and then the bacterial suspension is sucked by the nozzle 37 into the culture solution holding part 47 and heated by the heater 11 to culture the bacteria. The thus-obtained culture solution is supplied again by the nozzle 37 to the reaction vessel 44, followed by performing the steps after the step (S509) in the above embodiment, whereby the antimicrobial susceptibility test can be achieved.

In the Example, the amount of luminescence is expressed by the integration of the 60-sec photon count, and the unit is the amount of luminescence (a.u.). Since the amount of luminescence and the amount of ATP are in a proportional relationship, the increase in the amount of luminescence and the increase in the amount of ATP are to be expressed with the same implications.

The antimicrobial susceptibility testing device described above can be mainly applied to a test of sensitivity of a bacterium to a drug, and in particular to a test of sensitivity of an infectious disease-causing bacterium to a drug.

EXAMPLES

Hereinunder, the present invention will be described with reference to specific Examples, but the present invention is not limited to the Examples.

Example 1

In the Example, a antimicrobial susceptibility test by an ATP method was conducted using *Haemophilus influenzae*

(hereinafter referred to as *H. influenzae*) as bacterial cells. Sulfonamide was used as an antibody, and as the final concentration of the antibody, the two-fold serial dilutions from 0.125 to 512 µg/mL were prepared and used.

Benzalkonium chloride was used as an extraction liquid, and Lucifer HS set (Kikkoman) was used as a luminescence reagent.

First, *H. influenzae* was cultured one night on a chocolate agar medium under a carbon dioxide gas atmosphere of 5 to 10%, and on the next day, the colony was suspended in a Mueller-Hinton (hereinafter referred to as MH) medium to produce a bacterial suspension that was prepared to 0.5 McFarland. Next, in a plate in which 50 µL each of an MH medium with the antibody of the two-fold concentration of the final concentration was previously dispensed, 50 µL each of a bacterial suspension diluted 500-fold with the MH medium was dispensed to provide an AST panel.

By supplying a gas from the first gas feeding part 40 into the culture solution holding part 47 in the first plate 21 of the ATP examination culture plate 12, the gas atmosphere was prepared into a 5 to 10% of carbon dioxide gas atmosphere. 90 µL of the bacterial suspension of *H. influenzae* was taken from the AST panel using the first plate 21 in which the gas atmosphere was prepared.

The first plate 21 and the second plate 22 were joined via the joint portion 23. The temperature of the ATP examination culture plate 12 was kept at 37° C. by the heater 11 and after a certain period of time, 10 µL of the bacterial culture solution of *H. influenzae* was dispensed from the culture vessel in the first plate 21 into the reaction vessel in the second plate 22 in which the gas atmosphere was previously prepared to 5 to 10% carbon dioxide. Subsequently, 10 µL of the extraction liquid was dispensed from the extraction liquid holding part 43 into the reaction vessel, and then 50 µL of the luminescence reagent was dispensed from the luminescence reagent holding part 46 into the reaction vessel.

After dispensing the luminescence reagent, the amount of luminescence in the reaction vessel was detected by the optical detector 13. In the optical detector 13, photo-counting was performed for 1 minute, and the detected amount of luminescence RLU (relative light unit) was used as a measure of the amount of ATP.

Figure 9:
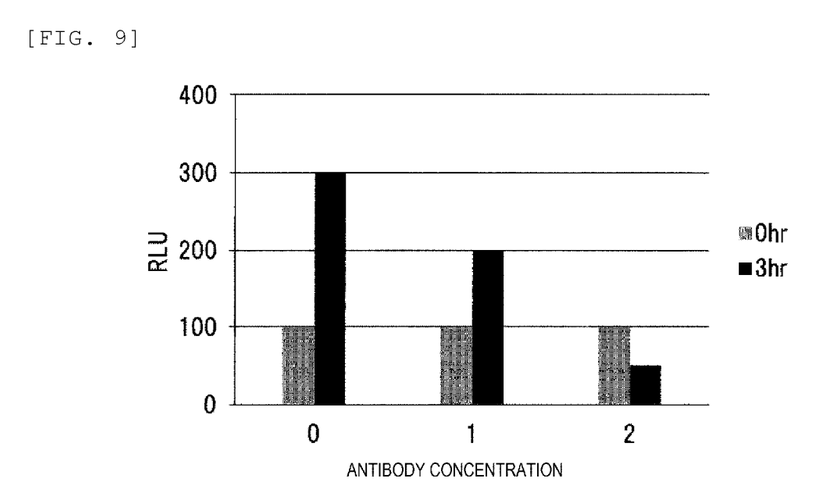
FIG. 9 It is a graph showing variations in amount of luminescence with time of culturing *H. influenzae*, for various concentrations of an antibody.

The variation in the amount of luminescence with the time of culturing *H. influenzae* is shown in FIG. 9.

At the start of the culture (0 hr), RLU is constant at all the concentrations of the antibody since the bacterial cell number in the culture solution is uniform. After culturing for a certain time (after 3 hr in FIG. 9, for example), RLU became higher than that at the start of the culture in an antibody (sulfonamide) concentration of 0 µg/mL, and thus it can be seen that the amount of ATP increased, that is, the bacteria grew. In an antibody (sulfonamide) concentration of 1 µg/mL, although the increment is smaller as compared with the antibody (sulfonamide) concentration of 0 µg/mL, RLU became higher than that at the start of the culture, and it can be seen that the bacteria grew. On the other hand, in an antibody (sulfonamide) concentration of 2 µg/mL, RLU became lower than that at the start of the culture, and it can be seen that the amount of the bacteria decreased by the action of the antibody (sulfonamide). That is, it can be determined that *H. influenzae* is resistant to the antibody (sulfonamide) at 1 µg/mL but has sensitivity at 2 µg/mL. In other words, it can be determined that *H. influenzae* has sensitivity to the antibody (sulfonamide) at least at 2 µg/mL or higher.

Example 2

Figure 10:
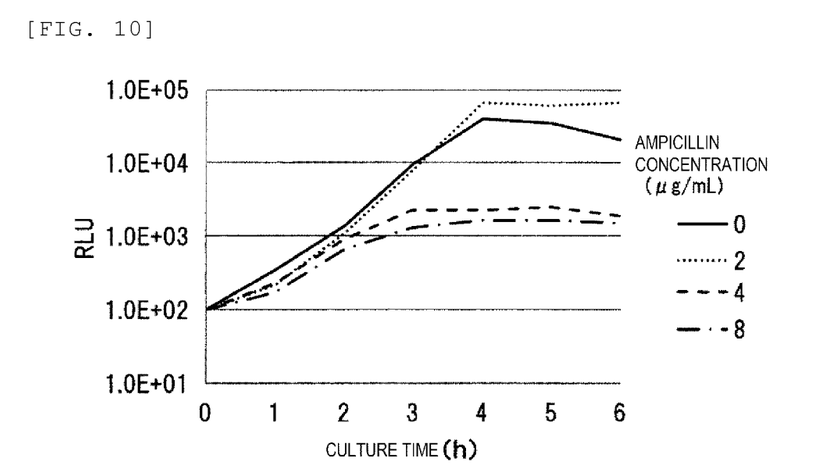
FIG. 10 It is a graph showing variations in amount of luminescence with time of culturing *E. coli*.

Example 2 was conducted in the same manner as in Example 1, except that *Escherichia coli* (ATCC25922 strain, hereinunder, *E. coli*) was used as bacterial cells, ampicillin was used as an antibody, and the gas atmosphere in the culture solution holding part 47 and the reaction vessel 44 of the ATP examination culture plate 21 was an air atmosphere. The antibody (ampicillin) concentration was 0, 2, 4, and 8 µg/mL. FIG. 10 shows the variation in the amount of luminescence, that is, the amount of ATP, with the time of culturing *E. coli*. When the ampicillin concentration was 0 µg/mL, RLU increased in an exponential manner from the start of the culture until 4 hours, and thereafter ran at a constant value. Also when the ampicillin concentration was 2 µg/mL, a similar trend was shown. On the other hand, when the ampicillin concentration was 4 µg/mL and 8 µg/mL, RLU increased from the start of the culture until 2 hours and thereafter ran at a constant value. The RLU value was as low as about ¹⁄₂₀ as compared with that at an ampicillin concentration of 0 µg/mL, and it can be seen that the growth of *E. coli* was suppressed by the action of ampicillin.

That is, it can be determined that *E. coli* is resistant to ampicillin at 2 µg/mL but has sensitivity at 4 µg/mL and 8 µg/mL. In other words, it can be determined that *E. coli* has sensitivity to ampicillin at least at 4 µg/mL or higher.

From the above, the following fact is confirmed. By continuously performing, with the gas atmosphere controlled, a step of culturing bacteria and a step of extracting ATP from the bacteria, a antimicrobial susceptibility test by an ATP method can easily be conducted for both of aerobic bacteria and anaerobic bacteria.

REFERENCE SIGNS LIST

11 . . . heater, 12 . . . ATP examination culture plate, 13 . . . optical detector, 14 . . . determination unit, 21 . . . first plate, 22 . . . second plate, 23 . . . joint portion, 31, 32, 33 . . . syringe, 34, 35, 36 . . . valve, 37, 38, 39 . . . nozzle, 40 . . . first gas feeding part, 41 . . . gas feeding path, 42 . . . extraction liquid bottle, 43 . . . extraction liquid holding part, 44 . . . reaction vessel, 45 . . . luminescence reagent bottle, 46 . . . luminescence reagent holding part, 47 . . . culture solution holding part, 48 . . . second gas feeding part, 430 . . . extraction liquid supplying unit, 431 . . . connection pipe, 460 . . . luminescence reagent supplying unit, 461 . . . connection pipe, 470 . . . culture solution supplying unit, 471 . . . connection pipe, S601 . . . ATP calculating unit, S602 . . . database storing unit, S603 . . . comparative computing unit

The invention claimed is:

1. A antimicrobial susceptibility testing device, comprising:
 an ATP examination culture plate that includes a reaction vessel, a reagent holding part for holding a reagent to be supplied to the reaction vessel, and a culture solution holding part for holding a culture solution to be supplied to the reaction vessel, and has a plurality of layers that can be joined and separated;
 a gas feeding path for feeding a gas into the ATP examination culture plate;
 a heater for heating the culture solution holding part,
 an optical detection unit for detecting luminescence inside the reaction vessel; and
 a determination unit for determining sensitivity of a bacterial strain contained in the culture solution to a drug based on the detection result of the optical detection unit, wherein when the plurality of layers of the ATP examination culture plate are joined, at least the culture solution holding part and the reaction vessel are in a sealed state while communicating with each other.

2. The antimicrobial susceptibility testing device according to claim 1, wherein the ATP examination culture plate includes a first plate including the reagent holding part and the culture solution holding part, a second plate including the reaction vessel, and a joint portion for joining the first plate and the second plate.

3. The antimicrobial susceptibility testing device according to claim 2, wherein the reagent holding part and the culture solution holding part are each provided with a nozzle on the reaction vessel side thereof, and the second plate is configured so that the nozzle can be inserted into the reaction vessel, and the reaction vessel is provided so as to keep a depth that allows the first plate and the second plate to be joined with the nozzles inserted therein.

4. The antimicrobial susceptibility testing device according to claim 2, wherein a first gas feeding part for feeding a gas into the culture solution holding part is connected to the first plate.

5. The antimicrobial susceptibility testing device according to claim 2, wherein the second plate has the gas feeding path that is connected to a second gas feeding part for feeding a gas into the reaction vessel.

6. The antimicrobial susceptibility testing device according to claim 3, wherein the length of the nozzle provided in the culture solution holding part is larger than the length of the nozzle provided in the reagent holding part.

7. The antimicrobial susceptibility testing device according to claim 1, wherein a plurality of the reaction vessels are connected to the gas feeding path.

8. A antimicrobial susceptibility testing kit, comprising:
   an ATP examination culture plate that includes a reaction vessel, a reagent holding part for holding a reagent to be supplied to the reaction vessel, and a culture solution holding part for holding a culture solution to be supplied to the reaction vessel, and has a plurality of layers that can be joined and separated; and
   a gas feeding path for feeding a gas into the ATP examination culture plate;
wherein when the plurality of layers of the ATP examination culture plate are joined, at least the culture solution holding part and the reaction vessel are in a sealed state while communicating with each other.

9. A antimicrobial susceptibility testing method, comprising:
   providing an ATP examination culture plate that includes a reaction vessel, a reagent holding part that holds a reagent to be supplied to the reaction vessel, and a culture solution holding part for holding a culture solution to be supplied to the reaction vessel, and has a plurality of layers, and bringing at least the culture solution holding part and the reaction vessel of the ATP examination culture plate into a sealed state in a manner that the culture solution holding part and the reaction vessel communicate with each other;
   supplying a gas from a gas feeding part into the ATP examination culture plate in which the plurality of layers are joined;
   heating the culture solution holding part in the sealed state by a heater to culture a bacterial suspension obtained by mixing a bacterium and a drug;
   supplying a culture solution obtained by culturing the bacterial suspension into the reaction vessel in the sealed state, while supplying the reagent from the reagent holding part into the reaction vessel;
   detecting luminescence inside the reaction vessel that holds a reaction solution of the culture solution and the reagent by an optical detection unit; and
   determining sensitivity of the bacterial strain contained in the culture solution to the drug by a determination unit based on the detection result of the optical detection unit.

10. The antimicrobial susceptibility testing method according to claim 9, wherein
   in the ATP examination culture plate, a first plate including the reagent holding part and the culture solution holding part and a second plate including the reaction vessel are provided so that the first plate and the second plate can be joined and separated, and
   the first plate and the second plate are joined via a joint portion before the bacterial suspension is cultured, and at least the culture solution holding part and the reaction vessel are brought into a sealed state while communicating with each other.

11. The antimicrobial susceptibility testing method according to claim 10, wherein the first plate and the second plate are joined with the nozzles provided in the reagent holding part and the culture solution holding part inserted in the reaction vessel.

12. The antimicrobial susceptibility testing method according to claim 11, wherein
   with the first plate and the second plate joined with each other, the culture solution is supplied from the nozzle provided in the culture solution holding part into the reaction vessel, while an ATP extraction reagent is supplied from the nozzle provided in the reagent holding part into the reaction vessel, and the culture solution and the ATP extraction reagent are mixed in the reaction vessel to extract ATP from the culture solution,
   subsequently a luminescence reagent that emits light by being mixed with ATP is supplied from the nozzle provided in the reagent holding part into the reaction vessel, and a culture solution held in the reaction vessel after the ATP extraction and the luminescence reagent are mixed, and
   the increase or decrease of the amount of luminescence in the reaction vessel that holds the luminescence reagent and the culture solution after the ATP extraction is detected by the optical detection unit.

13. The antimicrobial susceptibility testing method according to claim 12, wherein a gas is fed from the gas feeding part into at least the culture solution holding part and the reaction vessel of the ATP culture plate in which the first plate and the second plate are joined, and, with the gas atmosphere in the culture solution holding part and the reaction vessel controlled, the bacterial suspension is cultured in the culture solution holding part, and continuously, ATP in the culture solution of the bacterial suspension is extracted in the reaction vessel.

14. The antimicrobial susceptibility testing method according to claim 10, wherein, with the first plate and the second plate separated, the bacterial suspension held outside the ATP examination culture plate is supplied from the nozzle provided in the culture solution holding part into the culture solution holding part.

15. The antimicrobial susceptibility testing method according to claim 10, wherein, with the first plate and the second plate joined, the bacterial suspension held outside the ATP examination culture plate is once supplied into the reaction vessel, the bacterial suspension in the reaction vessel is sucked into the culture solution holding part, then the culture solution holding part is heated by the heater to culture the bacterial suspension, and the obtained culture solution is supplied again into the reaction vessel.

* * * * *